US012780764B2

(12) United States Patent
Bence et al.

(10) Patent No.: US 12,780,764 B2
(45) Date of Patent: Nov. 3, 2026

(54) APPARATUS AND METHOD FOR GAS-LIQUID SEPARATION OF A FISCHER-TROPSCH REACTOR OUTLET STREAM

(71) Applicant: JOHNSON MATTHEY DAVY TECHNOLOGIES LIMITED, London (GB)

(72) Inventors: Roger Kenneth Bence, London (GB); Jay Simon Clarkson, London (GB); Andrew James Coe, London (GB)

(73) Assignee: Johnson Matthey Davy Technologies Limited, London (GB)

( * ) Notice: Subject to any disclaimer, the term of this patent is extended or adjusted under 35 U.S.C. 154(b) by 174 days.

(21) Appl. No.: 18/730,959

(22) PCT Filed: Feb. 15, 2023

(86) PCT No.: PCT/GB2023/050343

§ 371 (c)(1),
(2) Date: Jul. 22, 2024

(87) PCT Pub. No.: WO2023/175293

PCT Pub. Date: Sep. 21, 2023

(65) Prior Publication Data

US 2025/0115533 A1 Apr. 10, 2025

(30) Foreign Application Priority Data

Mar. 15, 2022 (GB) ..................................... 2203544

(51) Int. Cl.
*C07C 7/00* (2006.01)
*C07C 7/09* (2006.01)

(52) U.S. Cl.
CPC ................ *C07C 7/005* (2013.01); *C07C 7/09* (2013.01)

(58) Field of Classification Search
CPC ............. C07C 7/005; C07C 7/09; C07C 7/00; B01J 8/005; C10G 2/34; C10G 2300/1022;
(Continued)

(56) References Cited

U.S. PATENT DOCUMENTS

| | | | |
|---|---|---|---|
| 5,021,148 A | 6/1991 | Meyer et al. |
| 5,033,915 A | 7/1991 | Albrecht |
| 12,618,011 B2 | 5/2026 | Claxton et al. |
| 2004/0266894 A1 | 12/2004 | Belmonte et al. |

(Continued)

FOREIGN PATENT DOCUMENTS

| | | |
|---|---|---|
| CL | 2023000640 A1 | 9/2023 |
| CL | 2023001118 A1 | 11/2023 |

(Continued)

*Primary Examiner* — Cephia D Toomer
(74) *Attorney, Agent, or Firm* — BakerHostetler

(57) ABSTRACT

Gas-liquid separation comprising a) feeding a product stream comprising a mixture of liquid and gaseous hydrocarbon products and water vapour; b) collecting the first liquid at a liquid outlet of the first vapour-liquid separator; c) discharging the first gas stream from a gas outlet of the first vapour-liquid separator; d) feeding the first cooled mixture from the first cooler into a second vapour-liquid separator; e) collecting the second liquid at a liquid outlet of the second vapour-liquid separator; f) discharging the second gas stream from a gas outlet of the second vapour-liquid separator; g) feeding the second gas stream from the gas outlet of the second vapour-liquid separator through a second cooler, h) feeding the second cooled mixture from the second cooler into a third vapour-liquid separator; i) collecting the third liquid at a liquid outlet; and j) discharging the third gas stream from a gas outlet.

20 Claims, 2 Drawing Sheets

(58) Field of Classification Search
CPC ...... C10G 2/00; B01D 5/00; B01D 2257/702; B01D 5/0003; B01D 5/0075; B01D 5/0081; B01D 5/009
See application file for complete search history.

(56) References Cited

U.S. PATENT DOCUMENTS

| | | | |
|---|---|---|---|
| 2011/0174683 | A1 | 7/2011 | Cui et al. |
| 2011/0210046 | A1 | 9/2011 | Tanaka et al. |
| 2018/0104616 | A1 | 4/2018 | Hall |
| 2021/0284915 | A1 | 9/2021 | Sun et al. |
| 2023/0383193 | A1 | 11/2023 | Baudner et al. |
| 2024/0025818 | A1 | 1/2024 | Aasberg-Petersen et al. |
| 2025/0059110 | A1 | 2/2025 | Paterson et al. |
| 2025/0100949 | A1 | 3/2025 | Paterson et al. |

FOREIGN PATENT DOCUMENTS

| | | | | |
|---|---|---|---|---|
| CL | 2023002160 | A1 | | 2/2024 |
| CL | 2024001854 | A1 | | 11/2024 |
| CL | 2024001898 | A1 | | 11/2024 |
| CN | 103170284 | A | | 6/2013 |
| CN | 103980930 | A | | 8/2014 |
| CN | 103666518 | B | | 10/2015 |
| CN | 107916127 | | * | 4/2018 |
| CN | 107916127 | A | | 4/2018 |
| CN | 112 094 663 | A | | 12/2020 |
| EP | 2 664 380 | A1 | | 11/2013 |
| JP | 2001-139961 | A | | 5/2001 |
| TH | 86511 | | * | 1/2022 |
| WO | 2010/038389 | A1 | | 4/2010 |
| WO | 2019/016757 | A1 | | 1/2019 |

* cited by examiner

APPARATUS AND METHOD FOR GAS-LIQUID SEPARATION OF A FISCHER-TROPSCH REACTOR OUTLET STREAM

FIELD OF THE INVENTION

The invention relates to apparatus and methods for gas-liquid separation, and in particular for separating a product stream that comprises hydrocarbon products and water vapour into separate liquid and gas fractions.

BACKGROUND OF THE INVENTION

It is known to produce oxygenated organic chemicals by means of chemical reaction. One well-known process for producing hydrocarbons at industrial scale is the Fischer-Tropsch process in which a mixture of carbon monoxide and hydrogen are reacted in the presence of a catalyst in a reactor to produce reaction products comprising hydrocarbons. The temperature and pressure used in the Fischer-Tropsch process are such that the reaction products initially discharged from the reactor are a mixture of liquid and gaseous hydrocarbon products and water vapour.

It is desirable to further process the reaction products to separate wax products from lighter hydrocarbon products. Typically, this further processing requires cooling the reactant products. A problem that can occur is that such cooling may cause the wax products to solidify and be deposited on components of the apparatus, for example in cooling apparatus such as condensers. This can lead to blockage of the apparatus necessitating the shut-down of the apparatus to allow for removal of the waxy deposits. Shutting down the reactor and restarting it leads to inefficiency, for example due to lost processing time and additional maintenance costs.

WO2019/016757 describes an apparatus and method for separating wax products from the products of an isothermal or adiabatic fixed bed reactor configured to carry out the Fischer-Tropsch process. WO2019/016757 attempts to address the problem of wax deposits by providing a first condenser and a second condenser that are in parallel fluid communication with the isothermal or adiabatic fixed bed reactor. In use, product from the Fischer-Tropsch process is first passed through the first condenser where it is cooled resulting in wax product solidifying and being collected in the first condenser. Once a predetermined amount of wax product has been collected in the first condenser, the product flow is switched to flow the product through the second condenser allowing the first condenser to be emptied of the wax product offline. Therefore, the use of the parallel first and second condensers permits continuous treatment of the product. However, the solution proposed in WO2019/016757 necessitates the use of parallel condensers, only one of which is ever in use at one time, which leads to inefficiency and additional complication, capital expenditure and maintenance costs.

The present invention seeks to tackle at least some of the problems associated with the prior art or at least to provide a commercially acceptable alternative solution thereto.

SUMMARY OF THE INVENTION

One aspect of the present disclosure is directed to a method comprising the steps of:

a) feeding a product stream comprising a mixture of liquid and gaseous hydrocarbon products and water vapour from a Fischer-Tropsch reactor into a first vapour-liquid separator inside which the product stream is separated into a first liquid comprising a first cut of the hydrocarbon products and a first gas stream comprising gaseous hydrocarbon products and water vapour;

b) collecting the first liquid at a liquid outlet of the first vapour-liquid separator;

c) discharging the first gas stream from a gas outlet of the first vapour-liquid separator and feeding the first gas stream through a first cooler to apply cooling to the first gas stream to condense a portion of the gaseous hydrocarbon products and water vapour to form a first cooled mixture;

d) feeding the first cooled mixture from the first cooler into a second vapour-liquid separator inside which the first cooled mixture is separated into a second liquid comprising a second cut of the hydrocarbon products and water, and a second gas stream comprising any remainder of the hydrocarbon products and water vapour;

e) collecting the second liquid at a liquid outlet of the second vapour-liquid separator;

f) discharging the second gas stream from a gas outlet of the second vapour-liquid separator;

g) feeding the second gas stream from the gas outlet of the second vapour-liquid separator through a second cooler to apply cooling to the second gas stream to condense a portion of the remainder of the hydrocarbon products and water vapour to form a second cooled mixture;

h) feeding the second cooled mixture from the second cooler into a third vapour-liquid separator inside which the second cooled mixture is separated into a third liquid comprising a third cut of the hydrocarbon products and water, and a third gas stream;

i) collecting the third liquid at a liquid outlet of the third vapour-liquid separator; and j) discharging the third gas stream from a gas outlet of the third vapour-liquid separator;

wherein the method further comprises feeding the second liquid and the third liquid into a single decanter inside which the second liquid and the third liquid are separated into liquid hydrocarbon products and water.

Another aspect of the present disclosure is directed to an apparatus coupled to the outlet of a Fischer-Tropsch reactor comprising:

- a first vapour-liquid separator comprising:
  - an inlet for receiving a product stream comprising hydrocarbon products and water vapour;
  - a liquid outlet for discharging a first liquid comprising a first cut of the hydrocarbon products; and
  - a gas outlet for discharging a first gas stream comprising a remainder of the hydrocarbon products and water vapour;
- a first cooler positioned in between the first vapour-liquid separator and a second vapour-liquid separator for cooling the first gas stream to form a first cooled mixture;
- the second vapour-liquid separator comprising:
  - an inlet for receiving the first cooled mixture;
  - a liquid outlet for discharging a second liquid comprising a second cut of the hydrocarbon products and water; and
  - a gas outlet for discharging a second gas stream comprising any remainder of the hydrocarbon products and water vapour;

a second cooler positioned in between the second vapour-liquid separator and a third vapour-liquid separator for cooling the second gas stream to form a second cooled mixture; and the third vapour-liquid separator comprising:

an inlet for receiving the second cooled mixture;

a liquid outlet for discharging a third liquid comprising a third cut of the hydrocarbon products and water; and a gas outlet for discharging a third gas stream;

wherein the apparatus comprises a single decanter for separating liquid hydrocarbon products from water, the single decanter comprising an inlet fluidly connected for receiving the second and third liquids from the second and third vapour-liquid separators, an outlet for liquid hydrocarbon products, and an outlet for water.

Another aspect of the present disclosure is directed to a method comprising the steps of:

a) feeding a product stream comprising a mixture of liquid and gaseous hydrocarbon products and water vapour from a Fischer-Tropsch reactor through a pre-cooler to cool the product stream to condense a portion of the hydrocarbon products and form a cooled product stream, and thereafter into a first vapour-liquid separator inside which the cooled product stream is separated into a first liquid comprising a first cut of the hydrocarbon products and a first gas stream comprising a remainder of the hydrocarbon products and water vapour;

b) collecting the first liquid at a liquid outlet of the first vapour-liquid separator;

c) discharging the first gas stream from a gas outlet of the first vapour-liquid separator and feeding the first gas stream through a first cooler to apply cooling to the first gas stream to condense a portion of the gaseous hydrocarbon products and water vapour to form a first cooled mixture;

d) feeding the first cooled mixture from the first cooler into a second vapour-liquid separator inside which the first cooled mixture is separated into a second liquid comprising a second cut of the hydrocarbon products and water, and a second gas stream comprising any remainder of the hydrocarbon products and water vapour;

e) collecting the second liquid at a liquid outlet of the second vapour-liquid separator;

f) discharging the second gas stream from a gas outlet of the second vapour-liquid separator;

g) feeding the second gas stream from the gas outlet of the second vapour-liquid separator through a second cooler to apply cooling to the second gas stream to condense a portion of the remainder of the hydrocarbon products and water vapour to form a second cooled mixture;

h) feeding the second cooled mixture from the second cooler into a third vapour-liquid separator inside which the second cooled mixture is separated into a third liquid comprising a third cut of the hydrocarbon products and water, and a third gas stream;

i) collecting the third liquid at a liquid outlet of the third vapour-liquid separator; and j) discharging the third gas stream from a gas outlet of the third vapour-liquid separator;

wherein the method further comprises feeding the second liquid and the third liquid into a single decanter inside which the second liquid and the third liquid are separated into liquid hydrocarbon products and water.

Another aspect of the present disclosure is directed to an apparatus coupled to a Fischer-Tropsch reactor comprising:

a first vapour-liquid separator comprising:

an inlet for receiving a product stream comprising hydrocarbon products and water vapour;

a liquid outlet for discharging a first liquid comprising a first cut of the hydrocarbon products, and a gas outlet for discharging a first gas stream comprising a remainder of the hydrocarbon products and water vapour;

a second vapour-liquid separator comprising:

an inlet for receiving the first gas stream, a liquid outlet for discharging a second liquid comprising a second cut of the hydrocarbon products and optionally water, and a gas outlet for discharging a second gas stream comprising any remainder of the hydrocarbon products and water vapour;

a first cooler positioned in between the first vapour-liquid separator and the second vapour-liquid separator for cooling the first gas stream before it reaches the second vapour-liquid separator;

a pre-cooler positioned upstream of the inlet of the first vapour-liquid separator for cooling the product stream before it reaches the first vapour-liquid separator a third vapour-liquid separator comprising:

an inlet for receiving the second gas stream, a liquid outlet for discharging a third liquid comprising a third cut of the hydrocarbon products and water, and a gas outlet for discharging a third gas stream; and a second cooler positioned in between the second vapour-liquid separator and the third vapour-liquid separator for cooling the second gas stream before it reaches the third vapour-liquid separator;

wherein the apparatus comprises a single decanter for separating liquid hydrocarbon products from water, the single decanter comprising an inlet fluidly connected for receiving the second and third liquids from the second and third vapour-liquid separators, an outlet for liquid hydrocarbon products, and an outlet for water.

DETAILED DESCRIPTION OF THE INVENTION

Figure 1:
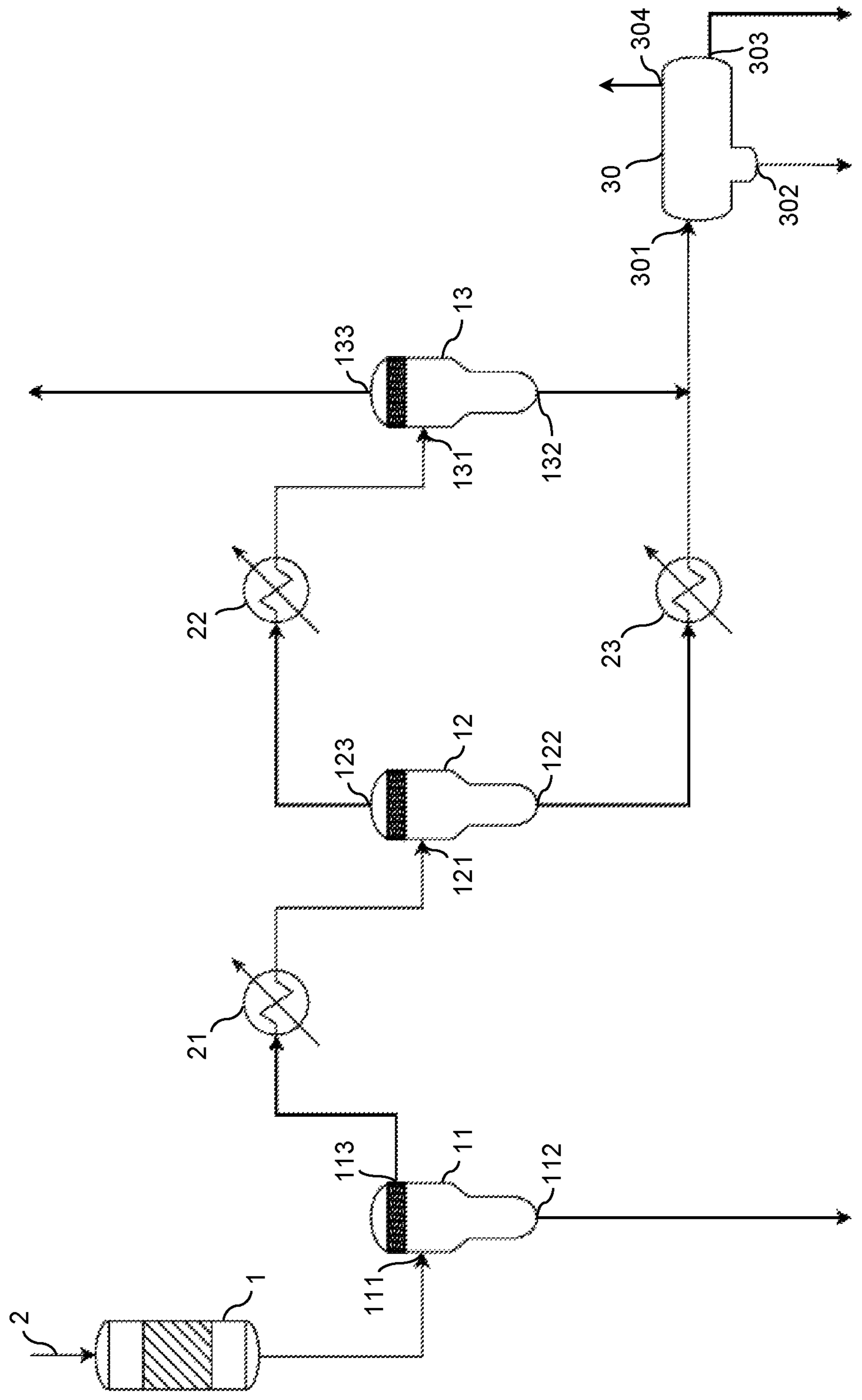
FIG. 1 is a diagram of an apparatus according to the present invention suitable for carrying out the method of the present invention.

In a first aspect, the present disclosure is directed to a method comprising the steps of.

a) feeding a product stream comprising a mixture of liquid and gaseous hydrocarbon products and water vapour from a Fischer-Tropsch reactor into a first vapour-liquid separator inside which the product stream is separated into a first liquid comprising a first cut of the hydrocarbon products and a first gas stream comprising gaseous hydrocarbon products and water vapour;

b) collecting the first liquid at a liquid outlet of the first vapour-liquid separator;

c) discharging the first gas stream from a gas outlet of the first vapour-liquid separator and feeding the first gas stream through a first cooler to apply cooling to the first gas stream to condense a portion of the gaseous hydrocarbon products and water vapour to form a first cooled mixture;

d) feeding the first cooled mixture from the first cooler into a second vapour-liquid separator inside which the first cooled mixture is separated into a second liquid comprising a second cut of the hydrocarbon products and water, and a second gas stream comprising any remainder of the hydrocarbon products and water vapour;

e) collecting the second liquid at a liquid outlet of the second vapour-liquid separator;

f) discharging the second gas stream from a gas outlet of the second vapour-liquid separator g) feeding the second gas stream from the gas outlet of the second vapour-liquid separator through a second cooler to apply cooling to the second gas stream to condense a portion of the remainder of the hydrocarbon products and water vapour to form a second cooled mixture;

h) feeding the second cooled mixture from the second cooler into a third vapour-liquid separator inside which the second cooled mixture is separated into a third liquid comprising a third cut of the hydrocarbon products and water, and a third gas stream;

i) collecting the third liquid at a liquid outlet of the third vapour-liquid separator; and j) discharging the third gas stream from a gas outlet of the third vapour-liquid separator;

wherein the method further comprises feeding the second liquid and the third liquid into a single decanter inside which the second liquid and the third liquid are separated into liquid hydrocarbon products and water.

Each aspect or embodiment as defined herein may be combined with any other aspect(s) or embodiment(s) unless clearly indicated to the contrary. In particular, any features indicated as being preferred or advantageous may be combined with any other feature indicated as being preferred or advantageous.

Advantageously, the method may allow for continuous operation. The method may beneficially reduce or substantially eliminate the build-up of deposits of wax products in the vapour-liquid separators and/or the coolers, for example by configuring the first vapour-liquid separator to function as a wax trap. The method may utilise at least three vapour-liquid separators and at least two coolers that are arranged in series. Such an arrangement may thereby avoid the need to duplicate equipment in a parallel configuration. In addition, such an arrangement may allow for two or more cuts (e.g. liquid fractions) to be separated from the gas stream in a controlled and flexible manner. In particular, such an arrangement may permit multistage separation and cooling to be applied to the product stream. In particular, the separation of the product stream may be carried out in stages, with a first stage functioning to remove wax products from the product stream while maintaining the temperature of the product stream sufficiently hot to prevent or at least substantially reduce the deposit of wax products on the walls or components of the apparatus. The staged cooling may be configured to separate desirable cuts of hydrocarbon products at temperatures where each cut is maintained as a mobile, liquid phase.

The term "vapour-liquid separator" as used herein may encompass a device configured to separate liquids from a gas. Examples of such vapour-liquid separators may be referred to as knockout pots, knockout drums or flash drums. The separation of the liquid from the gas within the vapour-liquid separator may be achieved by one or more mechanisms, used alone or in combination, including for example gravitational separation, velocity reduction, directional changes (including centrifugal separation), and impingement on elements such as vanes, demister pads and filter elements. The vapour-liquid separator may comprise a drum (or other vessel) that may be vertically or horizontally arranged.

The term "cooler" as used herein may encompass a device configured to applying cooling to a medium, in particular a gas and/or a liquid. Examples of such coolers include condensers and interchangers. The coolers may utilise, for example, one or more of gas cooling and liquid cooling. The liquid for cooling may comprise cooling water. The coolers may be configured as a produced water cooler so as to reduce or eliminate flash evaporation during pressure reduction of the liquid. The coolers may be configured as co-current coolers. The gas for cooling may comprise air. Alternatively, the gas may comprise a feed gas mixture for the Fischer-Tropsch reactor that produces, in use, the product stream.

Beneficially, the first and second coolers may use different heat exchange mediums. For example, the first cooler may use a feed gas mixture for the Fischer-Tropsch reactor as its heat exchange medium and the second cooler may use cooling water as its heat exchange medium. Beneficially, a gradual and staged cooling of the product stream may be enabled by using a relatively hot heat exchange medium in the first cooler and a relatively cold heat exchange medium in the second cooler. The second cooler may use a colder heat exchange medium (e.g. cooling water or air) because the remaining, lighter, hydrocarbons by that point will remain mobile and liquid at the lower wall temperatures in that portion of the apparatus, since the less mobile hydrocarbons (e.g. wax products and first cut products) have already been removed. The second cooler could beneficially be a combination of coolers in series. For example, an air-cooled heat exchanger followed by a cooling-water-cooled trim heat exchanger.

The first cut of the hydrocarbon products may comprise or consist of a wax product. The wax product may have a carbon chain length of C20 and higher. The term "wax product" as used herein may encompass a hydrocarbon having at least 20 carbon atoms. For example, the wax product may be a C20-C120 hydrocarbon, such as for example a C20-C40 hydrocarbon, a C20-C60 hydrocarbon, a C20-C80 hydrocarbon, or a C20-C110 hydrocarbon.

Beneficially, the first cut of the hydrocarbon products may be separated from the gas stream before the gas stream is passed through the first cooler. Advantageously, arranging for the first cut to comprise or consist of a wax product may allow for the wax product to be separated from the gas stream at an early stage of the process while the gas stream is still relatively hot, thereby reducing or substantially eliminating the likelihood of deposits of waxy hydrocarbon product blocking the apparatus, especially any cooler of the apparatus.

The method preferably comprises feeding the second liquid from the liquid outlet of the second vapour-liquid separator into the decanter inside which the second liquid is separated into liquid hydrocarbon products and water.

The term "decanter" as used herein may encompass a device configured for separating at least two liquid phases from each other, for example a hydrocarbon liquid phase from a liquid water phase. The decanter may be arranged horizontally, vertically or be spherical. The decanter may have means for venting a gas phase.

The method may comprise using a supplemental cooler to cool the second liquid before it reaches the decanter.

The second cut of the hydrocarbon products may be a heavier cut than the third cut of the hydrocarbon products. Optionally the second cut of the hydrocarbon products may comprise C5 to C30 hydrocarbons and the third cut of the hydrocarbon products may comprise C3 to C18 hydrocarbons.

The method may comprise feeding the third liquid from the liquid outlet of the third vapour-liquid separator into the decanter inside which the third liquid is separated into liquid hydrocarbon products and water.

The method comprises feeding the second liquid and the third liquid into a single decanter inside which the second liquid and the third liquid are separated into liquid hydrocarbon products and water. Beneficially, this may reduce the capital cost of the apparatus for performing the method since only a single decanter is required. A further advantage of the single decanter arrangement is that the second and third vapour-liquid separators need not be configured as three-phase separators, which would increase their complexity and cost and necessitate separate cooling of the liquid hydrocarbon products and water streams. In contrast, the present arrangement is able to use two-phase vapour liquid separators and a single cooler to cool the combined liquid stream from the second vapour-liquid separator prior to the single decanter.

The method may preferably further comprise using a supplemental cooler to cool the second liquid before it reaches the single decanter, optionally to a same temperature as that of the third liquid.

The supplemental cooler may beneficially use a colder heat exchange medium than the upstream coolers (e.g. cooling water or air) because the second liquid may comprise lighter hydrocarbons that remain mobile and liquid at lower wall temperatures and less mobile hydrocarbons (e.g. wax products and first cut products) have already been removed. The supplemental cooler may use co-current cooling with cooling water. Beneficially, this may help to avoid wall temperatures dropping too low within the supplemental cooler itself, which could cause trace amounts of wax carried over from the first vapour-liquid separator to deposit in the cooler.

The single decanter may be operated at a pressure of less than 10 bar(a); optionally less than 8 bar(a); optionally at 3 to 7 bar(a).

In some embodiments, the method may further comprise cooling the product stream before it reaches the first vapour-liquid separator by passing the product stream through a pre-cooler.

Advantageously, use of the pre-cooler may enable control of a feed temperature of the product stream to the first vapour-liquid separator. This may be particularly beneficial where the incoming product stream may vary in temperature. The Fischer-Tropsch process uses a catalyst that ages over time. The catalyst ageing may necessitate increasing the reactor temperature over time to compensate. Thus, the temperature of the product stream may vary, e.g. increase, over time within a set period. The use of the pre-cooler may allow for accommodation of a variable temperature product stream. In particular the use of the pre-cooler may help to avoid carry-over of wax products to the first cooler by providing sufficient pre-cooling to the product stream such that the first vapour-liquid separator can still adequately function to remove the wax products from the product stream.

Preferably, the first and/or second cooler may be cooled by a feed gas mixture for the Fischer-Tropsch reactor.

More preferably, the product stream may be cooled before it reaches the first vapour-liquid separator in a pre-cooler in heat exchange with a feed gas mixture for the Fischer-Tropsch reactor, preferably a feed gas mixture that has passed through the first cooler in heat exchange with the first gas mixture.

The temperature of the product stream exiting the reactor may be, for example, 205 to 240° C.

The pre-cooler (where present) may cool the product stream to a temperature in the range of 120 to 200° C., preferably 160 to 200° C.

The product stream may be fed to the first vapour-liquid separator at a temperature in the range of 120 to 200° C., preferably 160 to 200° C.

The first cooled mixture produced by the first cooler may have a temperature of, for example, 80 to 120° C.

The feed gas mixture may be heated to a temperature in the range of 100 to 220° C. in the first cooler.

The feed gas mixture may be heated to a temperature in the range of 190 to 220° C. in the pre-cooler (where present).

The first cooled mixture may be fed to the second vapour-liquid separator at a temperature in the range of 80 to 120° C.

The second cooled mixture produced by the second cooler may have a temperature of, for example, 40 to 60° C.

The supplemental cooler may cool the second liquid to a temperature of, for example, 40 to 60° C.

The second cooled mixture may be fed to the third vapour-liquid separator at a temperature in the range of 40 to 60° C.

Advantageously, the use of the pre-cooler and/or the first cooler and/or the second cooler and/or the supplemental cooler may enable controllable and flexible temperature control of the method. In particular, the temperatures of each of the vapour-liquid separators may be controllable independently of each other by co-ordinated use of the coolers, allowing for control of the temperature and thus the makeup of each liquid cut separated from the product stream. Beneficially this may enable prevention of carry-over of wax products to the first cooler as well as enabling the separation of desirable cuts of liquid hydrocarbon products without the need for distillation.

Another aspect of the present disclosure is directed to an apparatus coupled to the outlet of a Fischer-Tropsch reactor comprising:

- a first vapour-liquid separator comprising:
  - an inlet for receiving a product stream comprising hydrocarbon products and water vapour;
  - a liquid outlet for discharging a first liquid comprising a first cut of the hydrocarbon products; and
  - a gas outlet for discharging a first gas stream comprising a remainder of the hydrocarbon products and water vapour;
- a first cooler positioned in between the first vapour-liquid separator and a second vapour-liquid separator for cooling the first gas stream to form a first cooled mixture;
- the second vapour-liquid separator comprising:
  - an inlet for receiving the first cooled mixture;
  - a liquid outlet for discharging a second liquid comprising a second cut of the hydrocarbon products and water; and a gas outlet for discharging a second gas stream comprising any remainder of the hydrocarbon products and water vapour;

a second cooler positioned in between the second vapour-liquid separator and a third vapour-liquid separator for cooling the second gas stream to form a second cooled mixture; and the third vapour-liquid separator comprising:

an inlet for receiving the second cooled mixture;

a liquid outlet for discharging a third liquid comprising a third cut of the hydrocarbon products and water; and a gas outlet for discharging a third gas stream;

wherein the apparatus comprises a single decanter for separating liquid hydrocarbon products from water, the single decanter comprising an inlet fluidly connected for receiving the second and third liquids from the second and third vapour-liquid separators, an outlet for liquid hydrocarbon products, and an outlet for water.

The advantages and preferred features of the first aspect of the invention apply also to this aspect of the invention. The apparatus of this aspect may be used to perform the method of the first aspect.

Advantageously, the apparatus may be continually operated. The apparatus may be less prone to build-up of deposits of wax products in the vapour-liquid separators and/or the coolers. Beneficially the apparatus comprises at least three vapour-liquid separators and at least two coolers that are arranged in series. Such an arrangement may thereby avoid the need to duplicate equipment in a parallel configuration. In addition, such an arrangement may allow for one or more cuts (e.g. liquid fractions) to be separated from the product stream in a controlled and flexible manner. In particular, such an arrangement may permit multistage separation and cooling to be applied to the product stream. In particular, the separation of the product stream may be carried out in stages, with a first stage functioning to remove wax products from the product stream while maintaining the temperature of the product stream sufficiently hot to prevent or at least substantially reduce the deposit of wax products on the walls or components of the apparatus. The staged cooling may be configured to separate desirable cuts of hydrocarbon products at temperatures where each cut is maintained as a mobile, liquid phase.

The first cut of the hydrocarbon products may comprise or consist of a wax product.

Preferably the decanter comprises an inlet fluidly connected for receiving the second liquid from the second vapour-liquid separator, an outlet for liquid hydrocarbon products, and an outlet for water.

Preferably the apparatus further comprises a supplementary cooler positioned in between the second vapour-liquid separator and the decanter for cooling the second liquid before it reaches the decanter.

Preferably the decanter comprises an inlet fluidly connected for receiving the third liquid from the third vapour-liquid separator, an outlet for liquid hydrocarbon products, and an outlet for water.

The apparatus comprises a single decanter for separating liquid hydrocarbon products from water, the single decanter comprising an inlet fluidly connected for receiving the second and third liquids from the second and third vapour-liquid separators, an outlet for liquid hydrocarbon products, and an outlet for water.

In some embodiments the apparatus further comprises a supplementary cooler positioned in between the second vapour-liquid separator and the single decanter for cooling the second liquid, optionally to a same temperature as that of the third liquid, before it reaches the single decanter.

In some embodiments the apparatus further comprises a pre-cooler positioned upstream of the inlet of the first vapour-liquid separator for cooling the product stream before it reaches the first vapour-liquid separator.

Preferably the pre-cooler and the first cooler may be configured to be fed with a feed gas mixture for the Fischer-Tropsch reactor such that the product stream is cooled in heat exchange with the feed gas mixture after the feed gas mixture has passed through the first cooler in heat exchange with the first gas stream.

Each, vapour-liquid separator may be of a conventional cylindrical design. Preferably, one or more of the vapour-liquid separators may comprise a tapered body comprising an upper portion having a relatively larger internal diameter for receiving a cooled mixture and a lower portion having a relatively smaller internal diameter for collecting liquid, wherein the liquid outlet of the vapour-liquid separator is located in the lower portion having the relatively smaller internal diameter. The relative dimensions of the upper and lower portions may be sized, depending upon their duty using normal engineering practices. Preferably, the upper portion may have a length:diameter (L/D) ratio in the range of about 0.5 to 1.5:1 and the lower portion may have a length:diameter (L/D) ratio in the range of about 0.5 to 2.5:1, wherein the diameter of the lower portion is less than the diameter of the upper portion. The diameter of the lower portion may be in the range of 30% to 70% of the diameter of the upper portion. Each vapour-liquid separator may have a different L/D ratio and lower portion diameter, depending upon their duty, i.e. the amount of liquid being separated from vapour in the vessel. Beneficially, the tapered body and narrower lower portion may reduce and/or minimise the liquid residence time in the vapour-liquid separator which may in turn reduce or eliminate the hydrocarbon and water phases separating significantly upstream of the decanter.

Another aspect of the present disclosure is directed to a method comprising the steps of:

a) feeding a product stream comprising a mixture of liquid and gaseous hydrocarbon products and water vapour from a Fischer-Tropsch reactor through a pre-cooler to cool the product stream to condense a portion of the hydrocarbon products and form a cooled product stream, and thereafter into a first vapour-liquid separator inside which the cooled product stream is separated into a first liquid comprising a first cut of the hydrocarbon products and a first gas stream comprising a remainder of the hydrocarbon products and water vapour;

b) collecting the first liquid at a liquid outlet of the first vapour-liquid separator;

c) discharging the first gas stream from a gas outlet of the first vapour-liquid separator and feeding the first gas stream through a first cooler to apply cooling to the first gas stream to condense a portion of the gaseous hydrocarbon products and water vapour to form a first cooled mixture;

d) feeding the first cooled mixture from the first cooler into a second vapour-liquid separator inside which the first cooled mixture is separated into a second liquid comprising a second cut of the hydrocarbon products and water, and a second gas stream comprising any remainder of the hydrocarbon products and water vapour;

e) collecting the second liquid at a liquid outlet of the second vapour-liquid separator;

f) discharging the second gas stream from a gas outlet of the second vapour-liquid separator;

g) feeding the second gas stream from the gas outlet of the second vapour-liquid separator through a second cooler to apply cooling to the second gas stream to condense a portion of the remainder of the hydrocarbon products and water vapour to form a second cooled mixture;

h) feeding the second cooled mixture from the second cooler into a third vapour-liquid separator inside which the second cooled mixture is separated into a third liquid comprising a third cut of the hydrocarbon products and water, and a third gas stream;

i) collecting the third liquid at a liquid outlet of the third vapour-liquid separator; and j) discharging the third gas stream from a gas outlet of the third vapour-liquid separator;

wherein the method further comprises feeding the second liquid and the third liquid into a single decanter inside which the second liquid and the third liquid are separated into liquid hydrocarbon products and water.

The advantages and preferably features of the first aspect of the invention apply also to this aspect of the invention.

Preferably the product stream may be cooled before it reaches the first vapour-liquid separator in the pre-cooler in heat exchange with a feed gas mixture for the Fischer-Tropsch reactor that has passed through the first cooler in heat exchange with the first gas mixture.

Another aspect of the present disclosure is directed to an apparatus comprising a first vapour-liquid separator comprising:

- an inlet for receiving a first gas stream comprising hydrocarbon products and water vapour;
- a liquid outlet for discharging a first liquid comprising a first cut of the hydrocarbon products, and
- a gas outlet for discharging a second gas stream comprising a remainder of the hydrocarbon products and water vapour;

a second vapour-liquid separator comprising:

- an inlet for receiving the second gas stream,
- a liquid outlet for discharging a second liquid comprising a second cut of the hydrocarbon products and optionally water, and
- a gas outlet for discharging a third gas stream comprising any remainder of the hydrocarbon products and water vapour;

a first cooler positioned in between the first vapour-liquid separator and the second vapour-liquid separator for cooling the second gas stream before it reaches the second vapour-liquid separator;

and a pre-cooler positioned upstream of the inlet of the first vapour-liquid separator for cooling the first gas stream before it reaches the first vapour-liquid separator;

wherein the apparatus comprises a single decanter for separating liquid hydrocarbon products from water, the single decanter comprising an inlet fluidly connected for receiving the second and third liquids from the second and third vapour-liquid separators, an outlet for liquid hydrocarbon products, and an outlet for water.

The advantages and preferred features of the first aspect of the invention apply also to this aspect of the invention.

EXAMPLES

FIG. 1 shows a diagram of a first embodiment of apparatus according to the present invention suitable for carrying out the method of the present invention. The apparatus is configured for treating the reaction products output from a Fischer-Tropsch reactor 1. The Fischer-Tropsch reactor 1 is configured to receive a feedstock 2 and produce a product stream of reaction products by reaction of the feedstock in the presence of a catalyst. The Fischer-Tropsch reactor 1 may carry out the Fischer-Tropsch process in which a feedstock of carbon monoxide and hydrogen are reacted in the presence of a catalyst to produce reaction products comprising hydrocarbons. The product stream of reaction products initially discharged from the Fischer-Tropsch reactor 1 is a mixture of liquid and gaseous hydrocarbon products and water vapour. The temperature of the product stream exiting the Fischer-Tropsch reactor 1 may be, for example, 205 to 240° C.

The apparatus comprises a first vapour-liquid separator 11, a first cooler 21, a second vapour-liquid separator 12, a second cooler 22 and a third vapour-liquid separator 13 arranged in series. Further, a single decanter 30 is provided in series and downstream of the second and third vapour-liquid separators 12, 13.

The first vapour-liquid separator 11 comprises an inlet 111 for receiving the product stream that comprises the hydrocarbon products and water vapour output from the Fischer-Tropsch reactor 1, a liquid outlet 112 for discharging a first liquid comprising a first cut of the hydrocarbon products, and a gas outlet 113 for discharging a first gas stream comprising a remainder of the hydrocarbon products and water vapour. The first vapour-liquid separator 11 may be provided with a vane pack.

The first cooler 21 is positioned in between the first vapour-liquid separator 11 and the second vapour-liquid separator 12 and functions to cool the first gas stream to produce a first cooled mixture by condensing a portion of the gaseous hydrocarbon products and water vapour before it reaches the second vapour-liquid separator 12. The first cooler 21 may be configured to be fed with a feed gas mixture for the Fischer-Tropsch reactor 1 such that the first gas stream is cooled in heat exchange with the feed gas mixture.

The second vapour-liquid separator comprises an inlet 121 for receiving the first cooled mixture, a liquid outlet 122 for discharging a second liquid comprising a second cut of the hydrocarbon products and optionally water, and a gas outlet 123 for discharging a second gas stream comprising any remainder of the hydrocarbon products and water vapour.

The second cooler 22 is positioned in series in between the second vapour-liquid separator 12 and the third vapour-liquid separator 13 and functions to cool the second gas stream to produce a second cooled mixture by condensing a portion of the gaseous hydrocarbon products and water vapour before it reaches the third vapour-liquid separator 13.

The third vapour-liquid separator comprises an inlet 131 for receiving the second cooled mixture, a liquid outlet 132 for discharging a third liquid comprising a third cut of the hydrocarbon products and optionally water, and a gas outlet 133 for discharging a third gas stream comprising any remainder of the hydrocarbon products and water vapour.

The decanter 30 comprises an inlet 301 fluidly connected for receiving a mixed liquid feed comprising the second liquid from the second vapour-liquid separator 12 and the third liquid from the third vapour-liquid separator 13, an outlet 303 for liquid hydrocarbon products, and an outlet 302 for water. A gas outlet 304 may be provided for venting of off-gases. The decanter 30 is preferably a single decanter for the apparatus.

A supplemental cooler 23 is positioned in series in between the second vapour-liquid separator 12 and the decanter 30 to cool the second liquid before it is combined with the third liquid. An output from the supplemental cooler 23 is mixed with the third liquid output from the third vapour-liquid separator 13 before the mixed liquid feed is fed into the decanter 30 at inlet 301.

In use, the temperature of the product stream exiting the Fischer-Tropsch reactor 1 may be, for example, 205 to 240° C. The method comprises first feeding the product stream into the first vapour-liquid separator 11 (at inlet 111). The product stream may be fed to the first vapour-liquid separator 11 at a temperature in the range of 120 to 240° C., preferably 160 to 200° C. Inside the first vapour-liquid separator 11, the product stream is separated into the first liquid comprising the first cut of the hydrocarbon products and the first gas stream comprising the remainder of the hydrocarbon products and water vapour. The method also comprises collecting the first liquid at the liquid outlet 112 of the first vapour-liquid separator 11. The first vapour-liquid separator 11 may function as a wax trap to capture and remove from the product stream wax products.

The method also comprises discharging the first gas stream from the gas outlet 113 of the first vapour-liquid separator 11 and feeding the first gas stream through the first cooler 21 to apply cooling to the first gas stream to cool the first gas stream to produce the first cooled mixture by condensing a portion of the gaseous hydrocarbon products and water vapour. The first cooled mixture produced by the first cooler 21 may have a temperature of, for example, 80 to 120° C. The first cooler 21 may use the feed gas mixture for the Fischer-Tropsch reactor 1 to cool the first gas stream by heat exchange between the feed gas mixture and the first gas stream. The feed gas mixture may be heated to a temperature in the range of 100 to 220° C. in the first cooler 21.

The method also comprises feeding the first cooled mixture from the first cooler 21 into the second vapour-liquid separator 12 (at inlet 121). The first cooled mixture may be fed to the second vapour-liquid separator 12 at a temperature in the range of 80 to 120° C. Inside the second vapour-liquid separator 12 the first cooled mixture is separated into the second liquid comprising the second cut of the hydrocarbon products and optionally water, and the second gas stream comprising any remainder of the hydrocarbon products and water vapour.

The method also comprises collecting the second liquid at the liquid outlet 122 of the second vapour-liquid separator 12. The method also comprises discharging the second gas stream from the gas outlet 123 of the second vapour-liquid separator 12 and feeding the second gas stream through the second cooler 22 to apply cooling to the second gas stream to produce the second cooled mixture by condensing a portion of the gaseous hydrocarbon products and water vapour. The second cooled mixture produced by the second cooler 22 may have a temperature of, for example, 40 to 60° C. The second cooler 22 may use cooling water in heat exchange with the second gas stream.

The method also comprises feeding the second cooled mixture from the second cooler 22 into the third vapour-liquid separator 13 (at inlet 131). The second cooled mixture may be fed to the third vapour-liquid separator 13 at a temperature in the range of 40 to 60° C. Inside the third vapour-liquid separator 13 the second cooled mixture is separated into the third liquid comprising the third cut of the hydrocarbon products and optionally water, and the third gas stream comprising any remainder of the hydrocarbon products and water vapour. Further, collecting the third liquid at the liquid outlet 132 of the third vapour-liquid separator 13.

The third gas stream may be relatively dry and may, for example, comprise tails gas (e.g. unreacted reactants, $CO_2$, methane, ethane, etc.) that may be recycled to the Fischer-Tropsch reactor 1, or otherwise discharged from the apparatus.

The method also comprises feeding the second liquid and the third liquid into the decanter 30 (at inlet 301) inside which the second liquid and third liquid are separated into liquid hydrocarbon products that are collected at outlet 303 and water that is collected at outlet 302. Further, the second liquid may be passed through the supplemental cooler 23 to cool the second liquid, preferably to the same temperature as the third liquid, before reaching the decanter 30. The supplemental cooler 23 may cool the second liquid to a temperature of, for example, 40 to 60° C. The supplemental cooler 23 may use cooling water, preferably co-current cooling water, in heat exchange with the second liquid.

Figure 2:
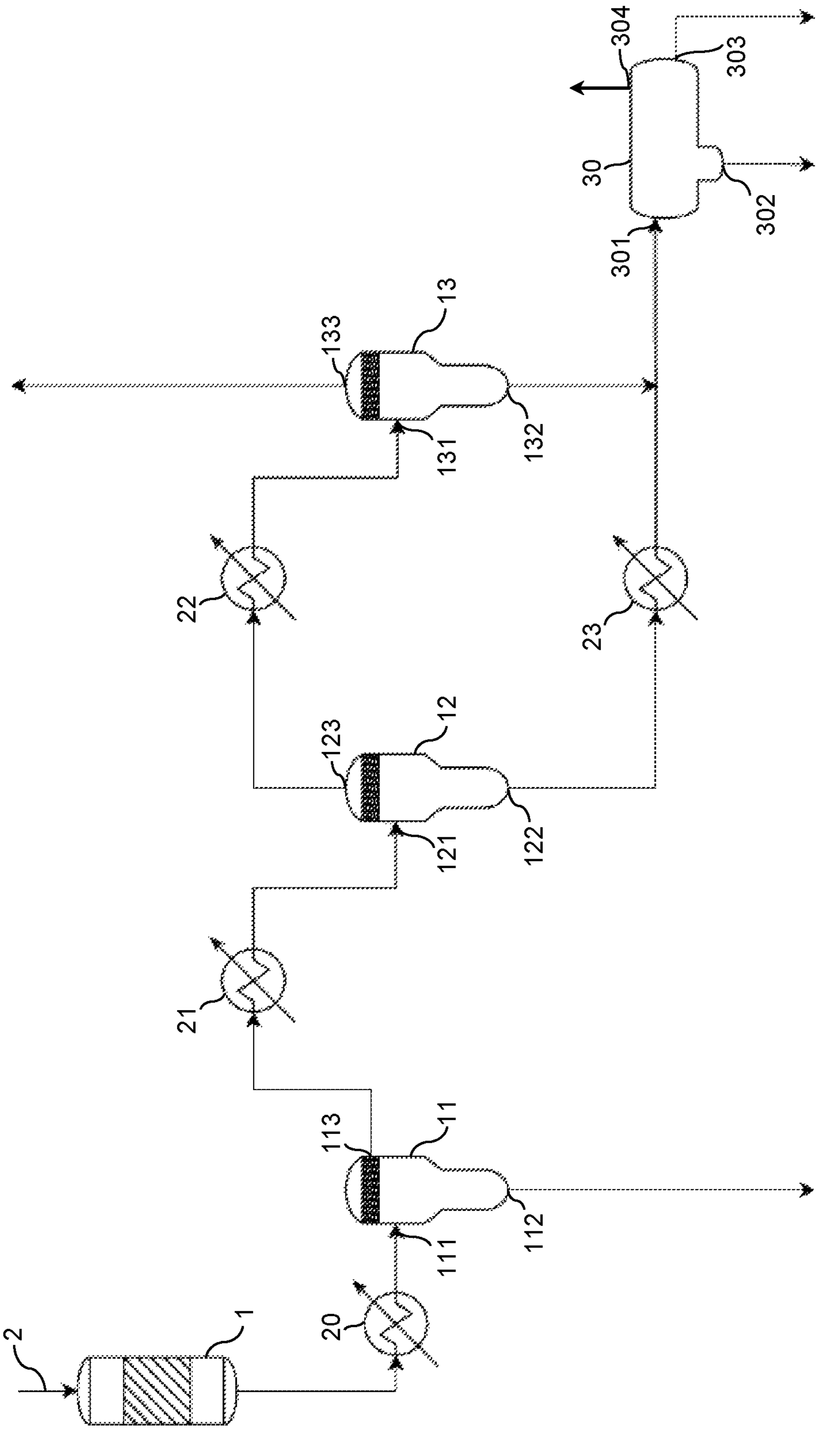
FIG. 2 is a diagram of a further apparatus according to the present invention suitable for carrying out the method of the present invention.

FIG. 2 shows a diagram of a second embodiment of apparatus according to the present invention suitable for carrying out the method of the present invention. Features of the second embodiment that are the same as the first embodiment have been given the same reference numerals in FIG. 2. These features will not be described in further detail and instead reference should be made to the description of the first embodiment above.

The apparatus of the second embodiment additionally comprises a pre-cooler 20. The pre-cooler 20 is positioned in series and in between the Fischer-Tropsch reactor 1 and the first vapour-liquid separator 11.

The pre-cooler 20 may be configured to be fed with a feed gas mixture for the Fischer-Tropsch reactor 1 such that the product stream from the reactor is cooled in heat exchange with the feed gas mixture. Preferably, this is after the feed gas mixture has passed through the first cooler 21 in heat exchange with the first gas stream. The feed gas mixture may be heated to a temperature in the range of 190 to 220° C. in the pre-cooler 20.

In use the method comprises feeding the product stream into the first vapour-liquid separator 11 (at inlet 111) via the pre-cooler 20 such that some cooling is applied to the product stream prior to it reaching the first vapour-liquid separator 11.

The use of the pre-cooler 20 may enable the product stream to be fed to the first vapour-liquid separator 11 at a temperature in the range of 120 to 200° C., preferably 160 to 200° C. and for this temperature range to be maintained even if the temperature of the product stream exiting the Fischer-Tropsch reactor 1 is increased to compensate for reactor catalyst ageing.

The remainder of the apparatus and method is as described in the first embodiment above.

It will be understood that the apparatus may comprise more than three vapour-liquid separators where desired. For example, additional pairs of a cooler and vapour-liquid separator may be added in series for further treatment of the fourth gas stream.

The foregoing detailed description has been provided by way of explanation and illustration and is not intended to limit the scope of the appended claims. Many variations in the presently preferred embodiments illustrated herein will be apparent to one of ordinary skill in the art and remain within the scope of the appended claims and their equivalents.

The invention claimed is:

1. A method comprising the steps of:

a) feeding a product stream comprising a mixture of liquid and gaseous hydrocarbon products and water vapour from a Fischer-Tropsch reactor into a first vapour-liquid separator inside which the product stream is separated into a first liquid comprising a first cut of the hydrocarbon products and a first gas stream comprising gaseous hydrocarbon products and water vapour;

b) collecting the first liquid at a liquid outlet of the first vapour-liquid separator;

c) discharging the first gas stream from a gas outlet of the first vapour-liquid separator and feeding the first gas stream through a first cooler to apply cooling to the first gas stream to condense a portion of the gaseous hydrocarbon products and water vapour to form a first cooled mixture;

d) feeding the first cooled mixture from the first cooler into a second vapour-liquid separator inside which the first cooled mixture is separated into a second liquid comprising a second cut of the hydrocarbon products and water, and a second gas stream comprising any remainder of the hydrocarbon products and water vapour;

e) collecting the second liquid at a liquid outlet of the second vapour-liquid separator;

f) discharging the second gas stream from a gas outlet of the second vapour-liquid separator;

g) feeding the second gas stream from the gas outlet of the second vapour-liquid separator through a second cooler to apply cooling to the second gas stream to condense a portion of the remainder of the hydrocarbon products and water vapour to form a second cooled mixture;

h) feeding the second cooled mixture from the second cooler into a third vapour-liquid separator inside which the second cooled mixture is separated into a third liquid comprising a third cut of the hydrocarbon products and water, and a third gas stream;

i) collecting the third liquid at a liquid outlet of the third vapour-liquid separator; and j) discharging the third gas stream from a gas outlet of the third vapour-liquid separator; wherein the method further comprises feeding the second liquid and the third liquid into a single decanter inside which the second liquid and the third liquid are separated into liquid hydrocarbon products and water, and wherein the second and third vapour-liquid separators are two-phase separators rather than three-phase separators.

2. The method of claim 1, wherein the first cut of the hydrocarbon products comprises or consists of a wax product having a carbon chain length of C20 and higher.

3. The method of claim 1, wherein the second cut of the hydrocarbon products is a heavier cut than the third cut of the hydrocarbon products; and optionally the second cut of the hydrocarbon products comprises C5 to C30 hydrocarbons and the third cut of the hydrocarbon products comprises C3 to C18 hydrocarbons.

4. The method of claim 1 further comprising using a supplemental cooler to cool the second liquid before it reaches the single decanter, optionally to a same temperature as that of the third liquid.

5. The method of claim 1, wherein the single decanter is operated at a pressure of less than 10 bar(a).

6. The method of claim 1 further comprising cooling the product stream before it reaches the first vapour-liquid separator by passing the product stream through a pre-cooler.

7. The method of claim 1, wherein the product stream is fed to the first vapour-liquid separator at a temperature in the range of 120 to 240° C.

8. The method of claim 1, wherein the first and/or second cooler is cooled by a feed gas mixture for the Fischer-Tropsch reactor.

9. The method of claim 1, wherein the product stream is cooled before it reaches the first vapour-liquid separator in a pre-cooler in heat exchange with a feed gas mixture for the Fischer-Tropsch reactor.

10. The method of claim 9, wherein the feed gas mixture is brought to a temperature in the range of 100 to 180° C. in the first cooler.

11. An apparatus comprising a Fischer-Tropsch reactor having an outlet and, coupled to the outlet of the Fischer-Tropsch reactor, further comprising:

a first vapour-liquid separator comprising:

an inlet for receiving a product stream comprising hydrocarbon products and water vapour;

a liquid outlet for discharging a first liquid comprising a first cut of the hydrocarbon products; and a gas outlet for discharging a first gas stream comprising a remainder of the hydrocarbon products and water vapour;

a first cooler positioned in between the first vapour-liquid separator and a second vapour-liquid separator for cooling the first gas stream to form a first cooled mixture;

the second vapour-liquid separator comprising:

an inlet for receiving the first cooled mixture;

a liquid outlet for discharging a second liquid comprising a second cut of the hydrocarbon products and water; and a gas outlet for discharging a second gas stream comprising any remainder of the hydrocarbon products and water vapour;

a second cooler positioned in between the second vapour-liquid separator and a third vapour-liquid separator for cooling the second gas stream to form a second cooled mixture; and the third vapour-liquid separator comprising:

an inlet for receiving the second cooled mixture;

a liquid outlet for discharging a third liquid comprising a third cut of the hydrocarbon products and water; and a gas outlet for discharging a third gas stream, wherein the apparatus comprises a single decanter for separating liquid hydrocarbon products from water, the single decanter comprising an inlet fluidly connected for receiving the second and third liquids from the second and third vapour-liquid separators, an outlet for liquid hydrocarbon products, and an outlet for water, and wherein the second and third vapour-liquid separators are two-phase separators rather than three-phase separators.

12. The apparatus of claim 11, wherein the first vapour-liquid separator is configured such that the first cut of the hydrocarbon products comprises or consists of a wax product.

13. The apparatus of claim 11 further comprising a supplementary cooler positioned in between the second vapour-liquid separator and the single decanter for cooling the second liquid, optionally to a same temperature as that of the third liquid, before it reaches the single decanter.

14. The apparatus of claim 11 further comprising a pre-cooler positioned upstream of the inlet of the first vapour-liquid separator for cooling the product stream before it reaches the first vapour-liquid separator.

15. The apparatus of claim 14, wherein the pre-cooler and the first cooler are configured to be fed with a feed gas mixture for the Fischer-Tropsch reactor such that the product stream is cooled in heat exchange with the feed gas mixture after the feed gas mixture has passed through the first cooler in heat exchange with the first gas stream.

16. The apparatus of claim 11, wherein one or more of the, vapour-liquid separators comprises a tapered body comprising an upper portion having a relatively larger internal diameter for receiving a cooled mixture and a lower portion having a relatively smaller internal diameter for collecting liquid, wherein the liquid outlet of the vapour-liquid separator is located in the lower portion having the relatively smaller internal diameter.

17. The method of claim 1, wherein the product stream is fed to the first vapour-liquid separator at a temperature in the range of 160 to 200° C.

18. The method of claim 1, wherein the single decanter is operated at a pressure of less than 8 bar(a).

19. The method of claim 1, wherein the single decanter is operated at a pressure of 3 to 7 bar(a).

20. The method of claim 1, wherein the product stream is cooled before it reaches the first vapour-liquid separator in a pre-cooler in heat exchange with a feed gas mixture for the Fischer-Tropsch reactor that has passed through the first cooler in heat exchange with the first gas mixture.

* * * * *